United States Patent
Hansmire

(10) Patent No.: US 8,877,282 B1
(45) Date of Patent: Nov. 4, 2014

(54) BRAND MARKETING AND POSITIVE ID USING INKLESS FINGERPRINT TECHNOLOGY

(76) Inventor: Kenny Hansmire, Fort Worth, TX (US)

(*) Notice: Subject to any disclaimer, the term of this patent is extended or adjusted under 35 U.S.C. 154(b) by 60 days.

(21) Appl. No.: 13/455,700

(22) Filed: Apr. 25, 2012

Related U.S. Application Data

(60) Provisional application No. 61/478,630, filed on Apr. 25, 2011.

(51) Int. Cl.
*A61B 5/103* (2006.01)
*A61B 5/117* (2006.01)
*B41K 1/00* (2006.01)

(52) U.S. Cl.
USPC .............................................. 427/1; 118/31.5

(58) Field of Classification Search
USPC .................. 427/1, 7, 145; 283/68; 118/31.5
See application file for complete search history.

(56) References Cited

U.S. PATENT DOCUMENTS

| | | | |
|---|---|---|---|
| 1,362,385 A * | 12/1920 | Bergman | 40/324 |
| 4,705,299 A | 11/1987 | Hedgcoth et al. | |
| 5,330,231 A | 7/1994 | Godfrey | |
| 5,419,589 A | 5/1995 | Fattore | |
| 5,454,600 A | 10/1995 | Floyd | |
| 5,928,708 A | 7/1999 | Hansmire | |
| 6,030,655 A * | 2/2000 | Hansmire et al. | 427/1 |
| 2002/0166477 A1 | 11/2002 | Arndt | |
| 2007/0037129 A1 | 2/2007 | Boyer | |

OTHER PUBLICATIONS

Nekoosa, How Inkless Works, Nov. 1, 2010, http://www.inklessfingerprintingsolutions.com/process.html. Accessed Nov. 14, 2013.*

* cited by examiner

*Primary Examiner* — Kelly M Gambetta
(74) *Attorney, Agent, or Firm* — Garvey, Smith, Nehrbass & North, L.L.C.; Gregory C. Smith; Julia M. FitzPatrick

(57) ABSTRACT

The apparatus and method or process of the present invention includes ID or fingerprinting kits to help brand a company's logo into a fingerprint. For many decades, companies have looked for unique ways to introduce their brand or logo into the marketplace. Companies have also helped law enforcement protect children by providing ID kits for distribution in communities. This apparatus and method or process looks to bring these two areas together by branding the company's logo into a fingerprint. The ID or fingerprint card must have a clear chemical coating then the non-visible brand or logo must also be printed on the card. This brand or logo may or may not include color. By applying a fingerprint activation solution to the chemically treated ID card, a fingerprint and logo or image will appear in the fingerprint.

14 Claims, 4 Drawing Sheets

BRAND MARKETING AND POSITIVE ID USING INKLESS FINGERPRINT TECHNOLOGY

CROSS-REFERENCE TO RELATED APPLICATIONS

This is a nonprovisional patent application of U.S. Provisional Patent Application Ser. No. 61/478,630, filed Apr. 25, 2011, which is hereby incorporated herein by reference.

Priority of U.S. Provisional Patent Application Ser. No. 61/478,630, filed Apr. 25, 2011, which is incorporated herein by reference, is hereby claimed.

BACKGROUND OF THE INVENTION

1. Field of the Invention

The present invention relates to fingerprinting. More particularly, the present invention relates to an apparatus and method or process which utilizes identification kits for fingerprints to help brand a company's logo into a fingerprint.

2. General Background of the Invention

For many decades companies have looked for unique ways to introduce their brand or logo into the marketplace. In that regard, companies have also helped law enforcement protect children by providing ID kits for distribution in communities, which would include a fingerprint of the child being identified. Because this child identification method has become quite common in the marketplace, the inventor of the technology in the present application has developed a unique product and method for combining a child's fingerprinting process which would also include a company's logo as part of the fingerprint product. It is foreseen that this process, although primarily intended for child fingerprinting, may be expanded to include persons of all ages.

The following U.S. patents are incorporated herein by reference:

TABLE

| U.S. PAT. NO. | TITLE | ISSUE DATE |
| --- | --- | --- |
| 1,362,385 | Paper Finger Bowl and Other Paper Vessel | Dec. 14, 1920 |
| 4,705,299 | Plastic Identity Card Capable of Providing an Inkless Fingerprint and Method of Developing Inkless Prints on Plastic Card | Nov. 10, 1987 |
| 5,330,231 | Greeting Card with Personal Identifier and Method of Producing | Jul. 19, 1994 |
| 5,419,589 | Apparatus and Method for Carrying Imprints of Body Portions | May 30, 1995 |
| 5,454,600 | Personal Identification Label | Oct. 3, 1995 |
| 5,928,708 | Positive Identification and Protection of Documents Using Inkless Fingerprint Methodology | Jul. 27, 1999 |
| 6,030,655 | Positive Identification and Protection of Documents Using Inkless Fingerprint Methodology | Feb. 29, 2000 |
| 2002/0166477 | Inkless Fingerprint Compound and Method | Nov. 14, 2002 |
| 2007/0037129 | Finger Angel Craft Kit and Personal Identification System and Device | Feb. 15, 2007 |

BRIEF SUMMARY OF THE INVENTION

The apparatus and method or process of the present invention solves the problems confronted in the art in a simple and straightforward manner. What is provided is an identification or fingerprinting kit and a method or process for utilizing identification kits to help brand a company's logo into a fingerprint of a person, such as a child. This product or process looks to bring two areas together by branding the company's logo into the fingerprint.

In the process, the identification card must include a clear chemical coating so that the non-visible brand logo must also be printed on the card. This brand or logo may or may not include color. By applying a fingerprint activation solution to the chemically treated ID card, a fingerprint and logo image will appear in the fingerprint. The method would include the following steps of providing a container having a pad with activation solution entrenched therein; providing a fingerprint card having at least one area of clear chemical coating, with an invisible company brand set therein; pressing a person's finger tip onto the pad to transfer a quantity of activation solution onto the person's finger tip; pressing the person's finger tip having the activation solution thereupon to the portion of the fingerprint card having the area of clear chemical coating; and lifting the fingertip from the card and exposing a fingerprint thereupon with the company brand exposed as part of the visible finger print.

The apparatus of the present invention would include a pad, an activation solution entrenched in a pad, a fingerprint card having at least one area of clear chemical coating, and an invisible company brand set in the area of the clear chemical coating that is capable of becoming visible upon application of the activation solution, for example with application via a fingertip.

In one embodiment, the apparatus of the present invention may include a pad; an activation solution entrenched in a pad; a fingerprint card having at least one area of clear chemical coating; invisible company brand set in the area of the clear chemical coating; a person's fingertip pressed onto the pad to transfer a quantity of activation solution onto the person's fingertip; the person's fingertip, with the activation solution thereupon to the portion of the fingerprint card having the area of clear chemical coating; and the person's fingerprint including the company brand exposed on the area of chemical coating after the fingertip has been lifted from the card.

In one embodiment of the present invention, the pad may be contained within a foil pouch. A Wet-Nap® (a registered trademark of Professional Disposables International, Inc.) is an example of a foil pouch and pad.

In one embodiment of the present invention, the activation solution could comprise a standard activation solution used in a conventional fingerprinting process.

In one embodiment of the present invention, the brand may be one of many different company brands.

In one embodiment of the present invention, the brand may appear in black and white or in various colors.

In one embodiment of the present invention the fingerprint card comprises multiple areas on the card for imprinting multiple fingerprints thereupon, each fingerprint exposing one or more company brands as desired.

The apparatus and method or process of the present invention can be used to establish the identity of children through a fingerprint program.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Reference is made to FIGS. 1-8, which illustrate the apparatus and method or process of the present invention.

Figure 1:
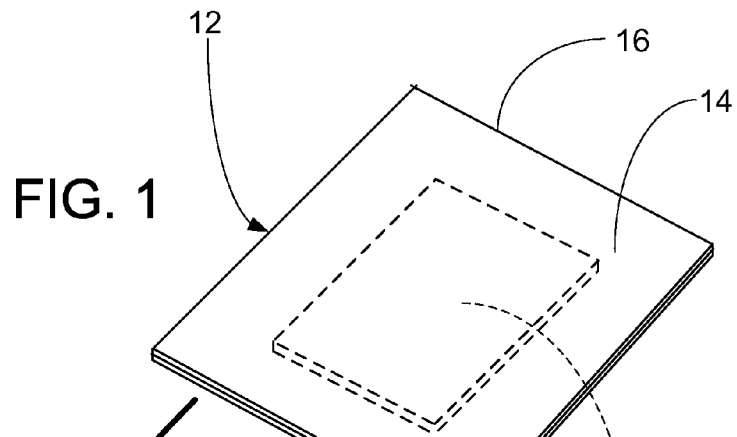
FIG. 1 illustrates an overall view of the cover of a foil pouch that would cover a pad with the activation solution thereupon.
Figure 2:
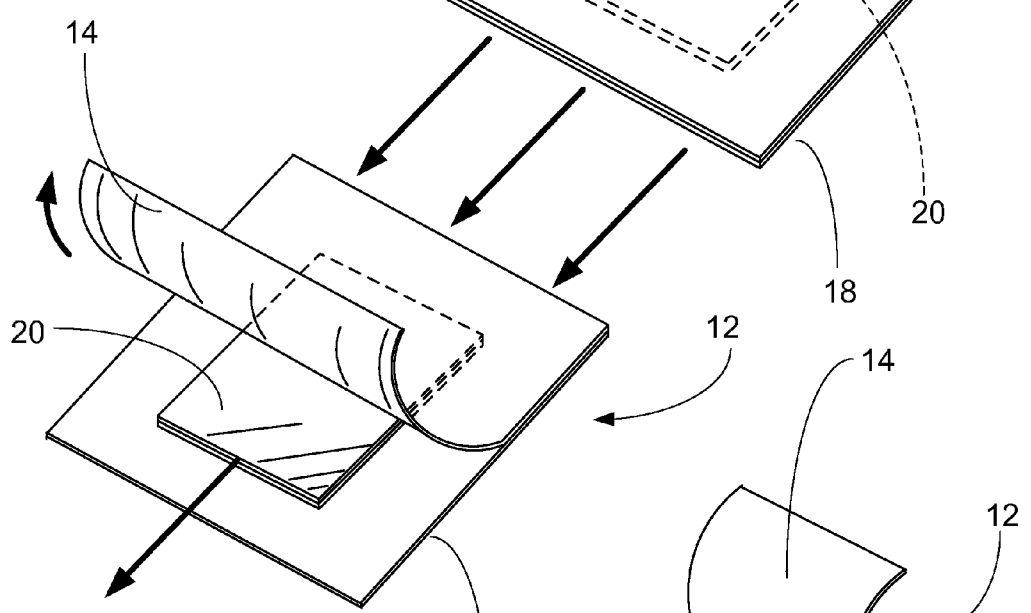
FIG. 2 illustrates the pad with the activation solution thereupon.
Figure 3:
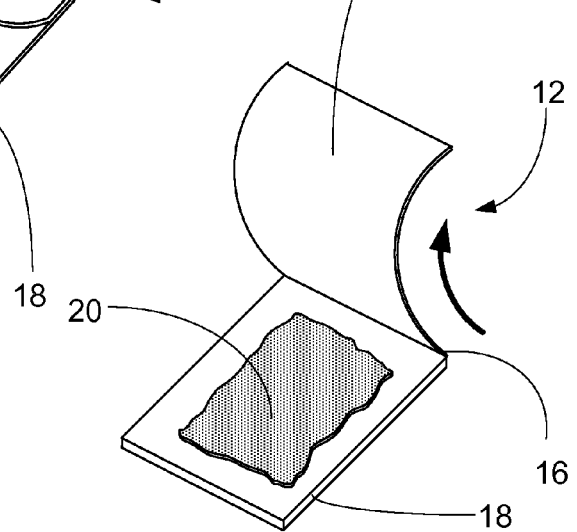
FIG. 3 illustrates an overall view of the composite pad illustrated in FIGS. 1 and 2.

In FIGS. 1 and 2, there is illustrated a foil pouch 12, an example of which is sold under the trademark Wet-Nap® (a registered trademark of Professional Disposables International, Inc.). Foil pouch 12 includes a flexible cover 14, as seen in FIG. 1, which would be hinged at a joint 16 to a base pad 18, of the type seen in FIG. 2. As illustrated in FIG. 3, base pad 18 has a construction so as to include a pad member 20 which would include an activation solution 22 imbedded within the pad 20, the function of which will be described further. The activation solution would be a chemical solution used in the current state of the art of fingerprinting.

Figure 4:
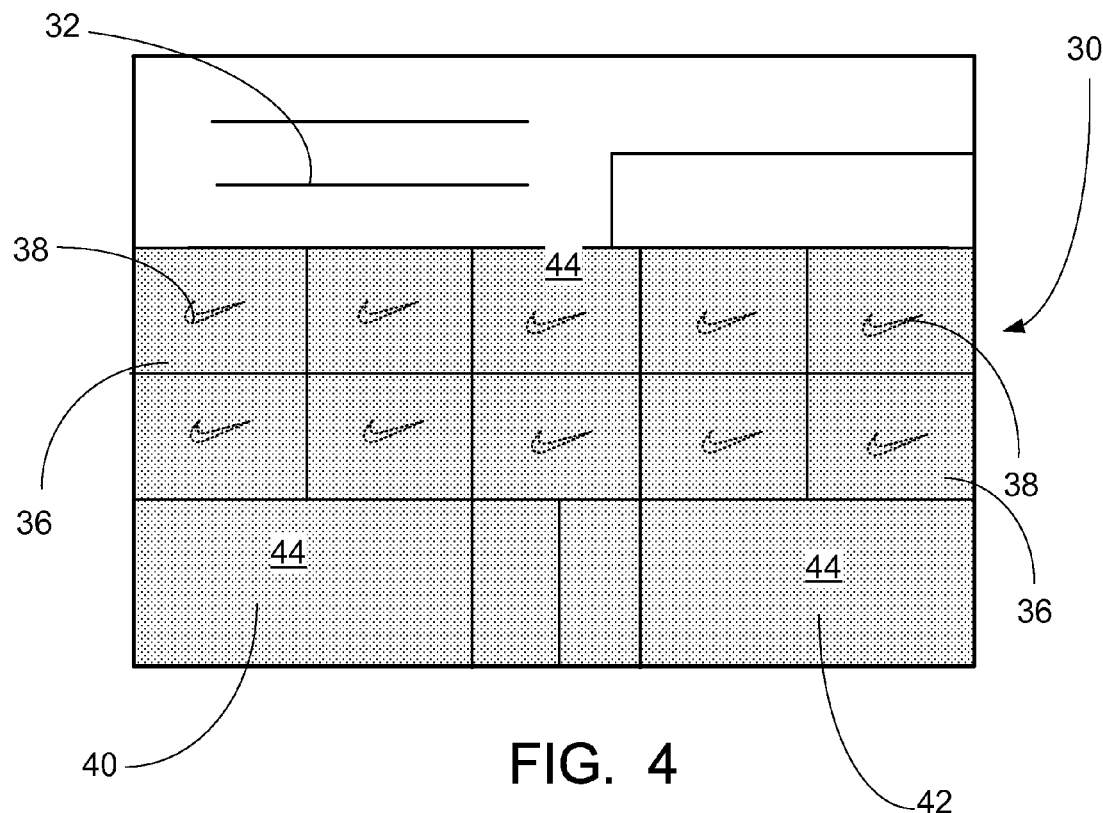
FIG. 4 illustrates an inkless fingerprint card having clear chemical coating on a plurality of squares for showing multiple fingerprints, wherein each square includes a non-visible or brand or logo contained in a square with the chemical coating.

Turning now to FIG. 4, there is illustrated an inkless fingerprint card 30 which includes an area 32 for identifying the person's name and address perhaps. The inkless fingerprint card is a flat card, as illustrated in top view in FIG. 4, which includes a plurality of squares 36, which would be a total of ten squares, each for accommodating the finger print of each of a person ten digits on a person's two hands. Each of the squares 36 would include a clear chemical coating 44, and below the coating 44 would have incorporated thereon a non-visible brand or logo 38 of the type which may include, for example, the famous "Swoosh" Nike® logo of Nike, Inc. (for footwear and athletic apparel for example). Further, in the lower portion of the card there is included a pair of spaces 40, 42 which would also include a clear chemical coating 44 therein for purposes which will be discussed further.

Figure 5:
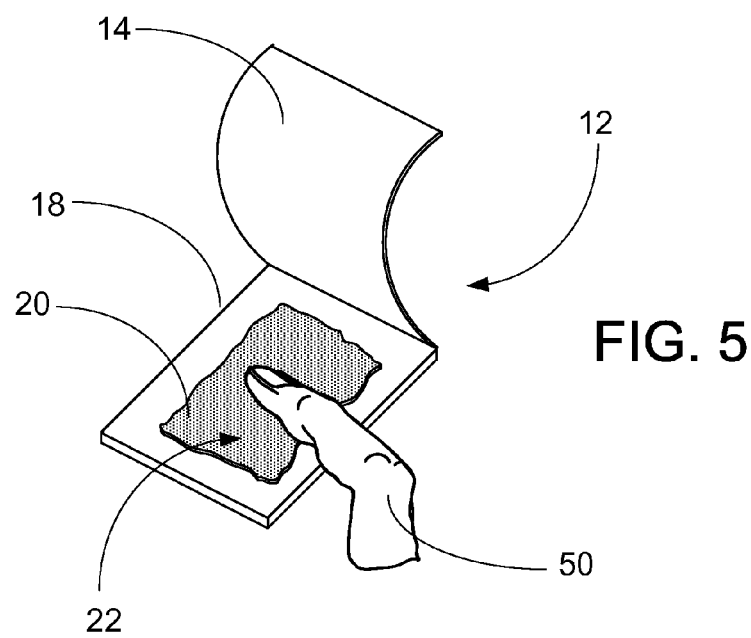
FIG. 5 illustrates a finger touching the activation solution identified in FIG. 2.
Figure 6:
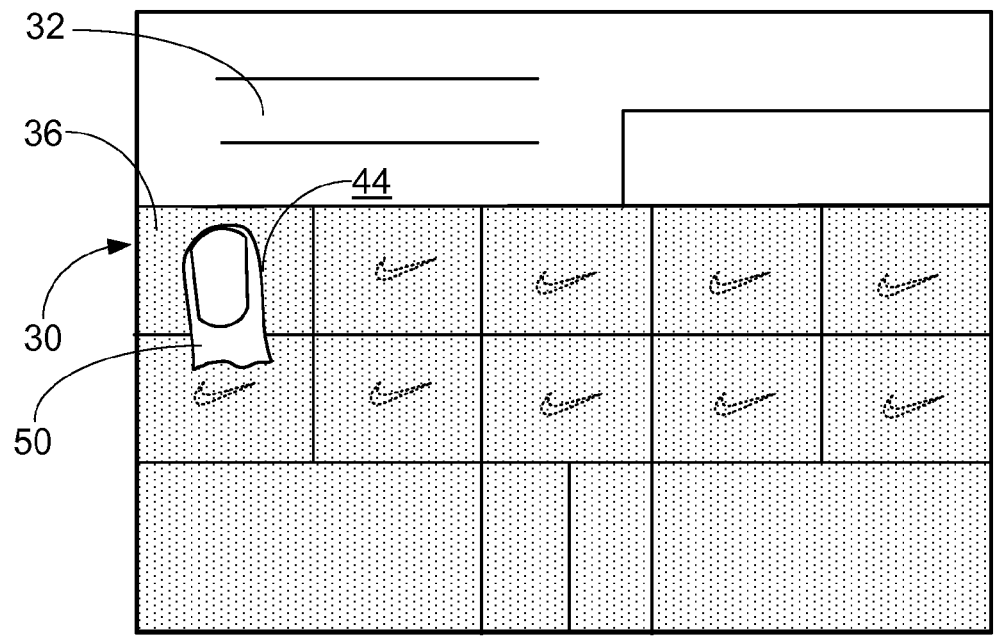
FIG. 6 illustrates a finger having activation solution pressing down on a square on the identification kit with a clear coating and the non-visible logo thereupon.
Figure 7:
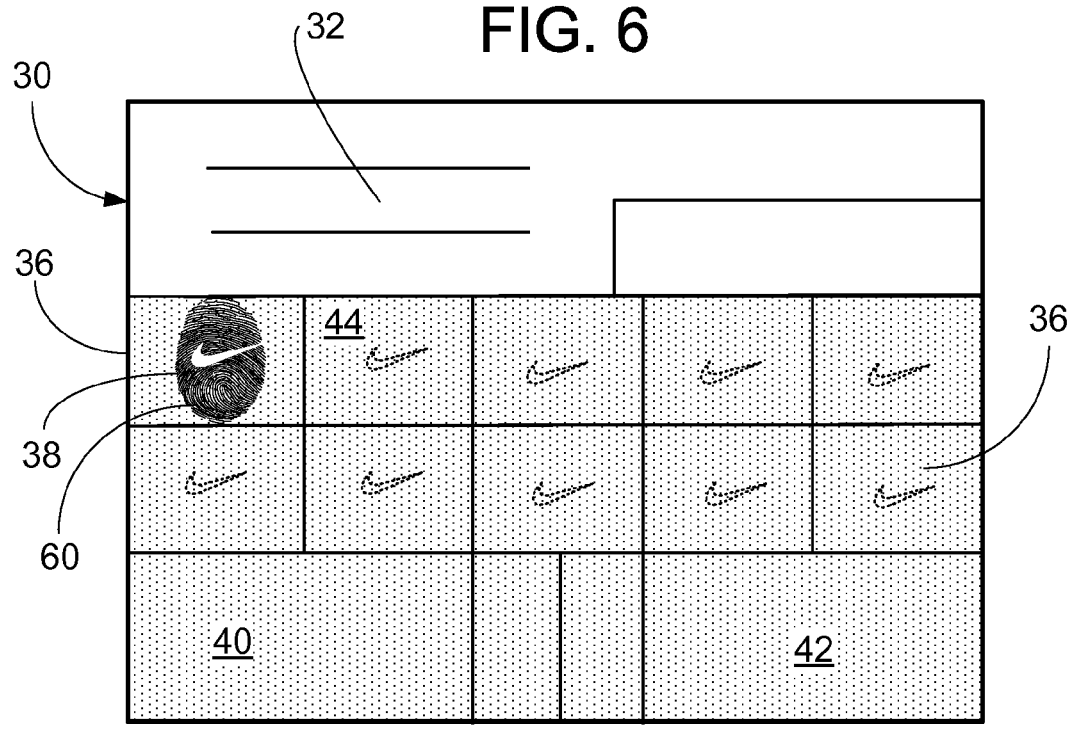
FIG. 7 illustrates the inkless fingerprint card with the finger removed so that the fingerprint appears with the company logo, such as the "Swoosh" of the Nike® logo (which is a registered trademark of Nike, Inc. for footwear and athletic apparel, for example), as part of the fingerprint.

Turning now to FIG. 5, a person's finger 50 is first placed upon the pad 18 which includes the activation solution 22. Next, a person's finger 50 has been moistened with the activation solution 22. Reference is now made to FIG. 6, where the person's finger 50 is then placed on the identification or fingerprint card 30 in one of the squares 36 so that the activation solution 22 on the finger 50 of the user makes contact with the clear chemical coating 44 on the square, and therefore, when the finger 50 is removed, as seen in FIG. 7, the person's fingerprint 60 is shown on the square. The chemical reaction of the activation solution 22 on the pad 18 also renders the formally invisible brand or logo now a visible brand, or logo 38, that appears on the fingerprint 60 as part of the overall fingerprint shown in square 36 of card 30. The logo 38 depicted in FIGS. 4, 6 and 7 is the "Swoosh" of the Nike® logo, which is a registered trademark of Nike, Inc. for footwear and athletic apparel, for example.

Figure 8:
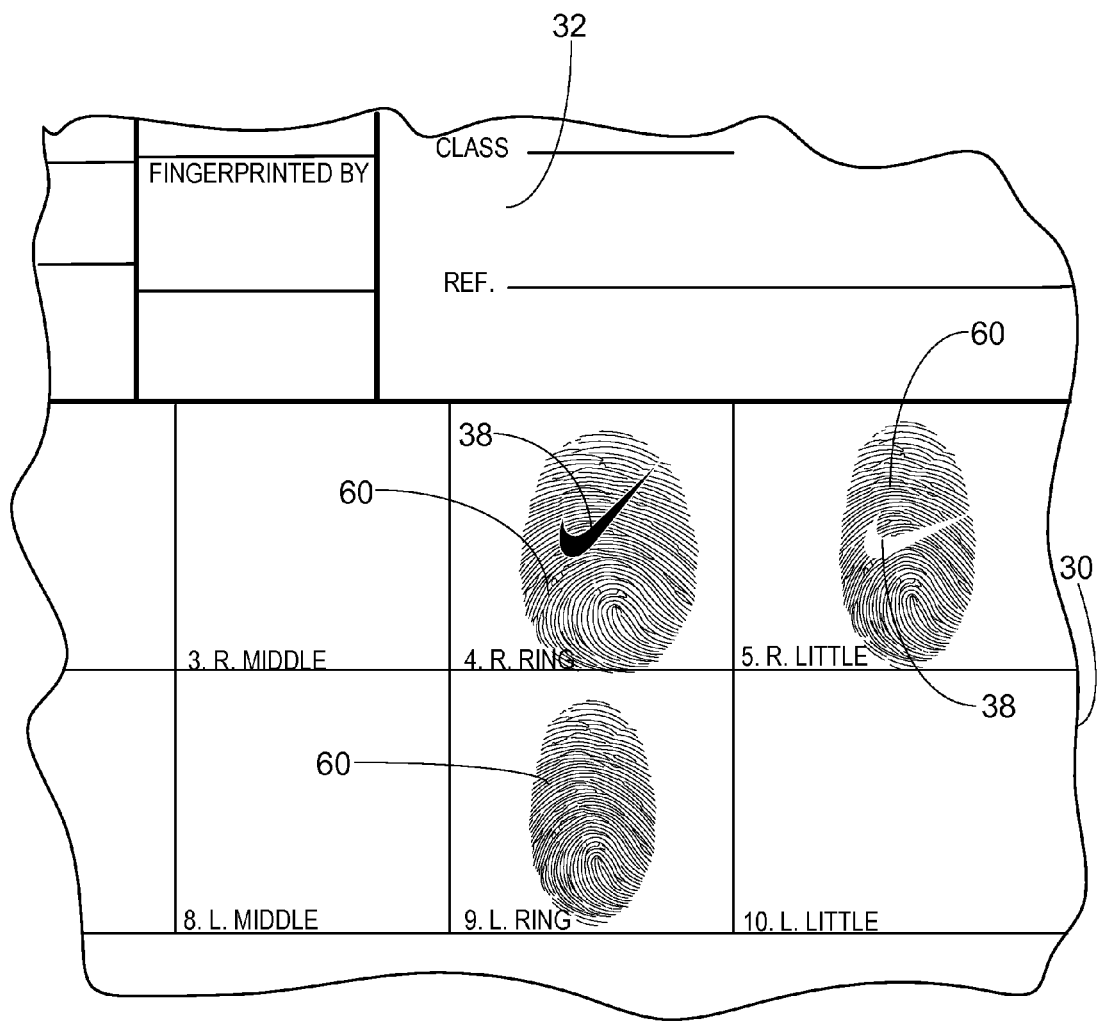
FIG. 8 illustrates an actual view of a fingerprint of a child as discussed in the various figures wherein the Nike® "Swoosh" logo (for footwear and athletic apparel, for example), is incorporated into the fingerprint.

As is clearly seen in FIG. 8, where a fingerprint 60 is left on a square 36 and when the finger is removed, the Nike® "Swoosh" logo 38 (for footwear and athletic apparel, for example), appears as part of the fingerprint. In the preferred embodiment, the logo 38 that appears in the fingerprint 60 may be in black and white or in various colors. Also seen in FIG. 8 there is a fingerprint 60 which appears in a square which does not include a logo and therefore there is no longer a logo which appears but a simple standard fingerprint.

PARTS LIST

The following is a list of parts and materials suitable for use in the present invention:

| PART NUMBER | DESCRIPTION |
| --- | --- |
| 12 | foil pouch |
| 14 | flexible cover |
| 16 | joint |
| 18 | base pad |
| 20 | pad member |
| 22 | activation solution |
| 30 | fingerprint card |
| 32 | area |
| 36 | squares |
| 38 | invisible/visible brand or logo |
| 40 | spaces |
| 42 | spaces |
| 44 | clear chemical coating |
| 50 | person's finger |
| 60 | person's fingerprint |

All measurements disclosed herein are at standard temperature and pressure, at sea level on Earth, unless indicated otherwise.

The foregoing embodiments are presented by way of example only; the scope of the present invention is to be limited only by the following claims.

The invention claimed is:

1. A method of brand marketing through positive identification, comprising the following steps:
   a. providing a pad with activation solution entrenched therein;
   b. providing a fingerprint card having at least one area of clear chemical coating, with an invisible company brand set therein;
   c. pressing a person's finger tip onto the pad to transfer a quantity of activation solution onto the person's finger tip;
   d. pressing the person's finger tip having the activation solution thereupon to the portion of the fingerprint card having the area of clear chemical coating;
   e. lifting the fingertip from the card and exposing a fingerprint thereupon with the company brand exposed as part of the visible finger print, wherein the activation solution renders the formally invisible company brand now a visible brand.

2. The method in claim 1, wherein the fingerprint card includes multiple areas of the card with clear chemical coating to receive a plurality of fingerprints thereupon.

3. The method in claim 1, wherein the company brand may be any number of different company brands which serve to advertise the company as the brand is exposed on the fingerprint.

4. The method in claim 1, wherein the method is utilized primarily to establish the identity of children through a fingerprint program.

5. An apparatus to expose a company brand as part of a fingerprint, comprising:
  a. a pad;
  b. activation solution entrenched in a pad;
  c. a fingerprint card having at least one area of clear chemical coating;
  d. invisible company brand set in the area of the clear chemical coating;
  e. a person's finger tip pressed onto the pad to transfer a quantity of activation solution onto the person's finger tip;
  f. the person's finger tip, with the activation solution thereupon to the portion of the fingerprint card having the area of clear chemical coating;
  g. the person's fingerprint including the company brand exposed on the area of chemical coating after the fingertip has been lifted from the card.

6. The apparatus in claim 5, wherein the pad is contained within a foil pouch.

7. The apparatus in claim 5, wherein the activation solution comprises a standard activation solution used in a conventional fingerprinting process.

8. The apparatus in claim 5, wherein the brand may be one of many different company brands.

9. The apparatus in claim 5, wherein the fingerprint card comprises multiple areas on the card for imprinting multiple fingerprints thereupon, each fingerprint exposing one or more company brands as desired.

10. The apparatus in claim 5, wherein the apparatus is utilized primarily to establish the identity of children through a fingerprint program.

11. The apparatus in claim 5, wherein the brand may appear in black and white or in various colors.

12. A brand marketing identification or fingerprinting kit for branding a company's logo or mark into a fingerprint of a person, comprising:
  a) a pouch for housing a base pad;
  b) the base pad including a pad member;
  c) the pad member including a fingerprinting activation solution imbedded within the pad member, for application to a person's finger tip;
  d) a card including at least one area of clear chemical coating, wherein the area of clear chemical coating is for receiving contact from a person's finger tip containing the fingerprinting activation solution for producing a fingerprint on the card; and
  e) a non-visible brand identification imprinted on the card in the area of clear chemical coating, wherein the non-visible brand identification is capable of becoming visible upon activation by the fingerprinting activation solution, so that when contact from a person's finger tip is applied to the area of clear chemical coating the brand identification is branded into the resulting fingerprint.

13. The brand marketing identification or fingerprinting kit of claim 12 wherein the card includes a total of ten areas of clear chemical coating for accommodating the fingerprint of each of a person's ten fingers, wherein there are a total of ten non-visible brand identifications imprinted on the card in the areas of clear chemical coating, for branding the brand identifications into ten fingerprints of a person.

14. The brand marketing identification or fingerprinting kit of claim 12, wherein the pouch includes a flexible cover hingedly connected at a joint to the base pad.

* * * * *